(12) United States Patent
Tanaami et al.

(10) Patent No.: US 7,858,045 B2
(45) Date of Patent: Dec. 28, 2010

(54) CHEMICAL REACTION CARTRIDGE AND METHOD OF USING SAME

(75) Inventors: Takeo Tanaami, Musashino (JP); Saya Satou, Musashino (JP); Hisao Katakura, Musashino (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 368 days.

(21) Appl. No.: 11/528,535

(22) Filed: Sep. 28, 2006

(65) Prior Publication Data

US 2007/0077170 A1 Apr. 5, 2007

(30) Foreign Application Priority Data

Sep. 30, 2005 (JP) ............................. 2005-287470

(51) Int. Cl.
 *B01L 3/00* (2006.01)
(52) U.S. Cl. ........................ 422/102; 422/58; 422/61; 422/100; 422/101; 436/177; 436/178; 436/180
(58) Field of Classification Search .................... 422/58, 422/61, 82.05, 100–102; 436/174–180
See application file for complete search history.

(56) References Cited

U.S. PATENT DOCUMENTS

| | | | | |
|---|---|---|---|---|
| 4,065,263 | A | * | 12/1977 | Woodbridge, III ............ 422/57 |
| 5,288,463 | A | * | 2/1994 | Chemelli ...................... 422/58 |
| 5,593,804 | A | * | 1/1997 | Chemelli et al. .............. 430/30 |
| 5,804,141 | A | * | 9/1998 | Chianese ...................... 422/63 |
| 5,863,502 | A | * | 1/1999 | Southgate et al. ............. 422/58 |
| 5,932,799 | A | * | 8/1999 | Moles ........................ 73/53.01 |

(Continued)

FOREIGN PATENT DOCUMENTS

DE 10222478 A1 4/2003

(Continued)

OTHER PUBLICATIONS

European Search Report dated Feb. 12, 2008, issued in corresponding European Patent Application No. 07024682.

(Continued)

*Primary Examiner*—Jill Warden
*Assistant Examiner*—Dwayne K Handy
(74) *Attorney, Agent, or Firm*—Westerman, Hattori, Daniels & Adrian, LLP (57) ABSTRACT

A cartridge adaptable to various measurement forms is provided. A sample is injected into a well via an injection path. When a roller while kept pressed into contact with the cartridge is rotated rightward, the sample held in the well, and liquid solvent held in a well are caused to reach a well via flow paths, respectively, thereby mixing the sample with the liquid solvent. A mixed liquid is branched into flow paths, respectively, to thereby reach wells, respectively, and reagents preheld in wells, respectively, are caused to flow into the wells, respectively. Next, temperatures in the wells, respectively, are controlled, thereby executing DNA amplification. Then, PCR by-products as amplified in the wells, respectively, are transferred as far as a position in the vicinity of an electrode via flow paths. Subsequently, a voltage is applied across the electrode as a negative electrode, and an electrode as a positive electrode via a drawing electrode and a drawing electrode, to thereby cause the PCR by-products to undergo electrophoresis.

20 Claims, 9 Drawing Sheets

U.S. PATENT DOCUMENTS

| | | | |
|---|---|---|---|
| 6,319,469 B1 * | 11/2001 | Mian et al. | 422/64 |
| 6,426,230 B1 | 7/2002 | Feistel | |
| 6,645,758 B1 * | 11/2003 | Schnipelsky et al. | 435/287.2 |
| 6,692,700 B2 * | 2/2004 | Handique | 422/100 |
| 7,056,475 B2 * | 6/2006 | Lum et al. | 422/100 |
| 7,198,759 B2 * | 4/2007 | Bryning et al. | 422/100 |
| 2004/0018116 A1 * | 1/2004 | Desmond et al. | 422/58 |
| 2004/0137607 A1 | 7/2004 | Tanaami et al. | |
| 2004/0254559 A1 | 12/2004 | Tanaami et al. | |
| 2005/0019814 A1 | 1/2005 | Laugharn, Jr. et al. | |
| 2005/0153430 A1 | 7/2005 | Ohtaka | |

FOREIGN PATENT DOCUMENTS

| | | |
|---|---|---|
| DE | 10222478 A1 | 12/2003 |
| JP | 09-262084 A | 10/1997 |
| JP | 2944216 B2 | 8/1999 |
| JP | 2002-218998 A | 8/2002 |
| JP | 2003-156475 A | 5/2003 |
| JP | 2004-226068 A | 8/2004 |
| JP | 2005-021866 A | 1/2005 |
| JP | 2005-024483 A | 1/2005 |
| JP | 2005-037368 A | 2/2005 |
| JP | 2005-164296 A | 6/2005 |
| WO | WO 01/07892 A1 | 2/2001 |
| WO | WO 01/07892 A1 | 2/2001 |

OTHER PUBLICATIONS

European Search Report dated Feb. 20, 2008, issued in corresponding European Patent Application No. 07024681.

European Search Report dated Mar. 15, 2007, Application No. 06017986.8-2113.

European Search Report dated May 29, 2007, Application No. 06017986.8-2113.

Office Action dated Aug. 9, 2010, for Japanese Patent Application No. 2005-287470.

Office Action dated Apr. 20, 2010, for Japanese Patent Application No. 2005-287470.

* cited by examiner

CHEMICAL REACTION CARTRIDGE AND METHOD OF USING SAME

FIELD OF THE INVENTION

The invention relates to a chemical reaction cartridge capable of causing deformation to occur thereto upon application of an external force thereto, so as to transfer substances contained therein, thereby causing chemical reaction to proceed, and a method of using the same.

BACKGROUND OF THE INVENTION

A chemical reaction cartridge that can cause chemical reaction to proceed by transferring substances contained therein, due to deformation occurring thereto, upon application of an external force thereto, has been under development.
[Patent Document 1] JP 2004-226068 A

SUMMARY OF THE INVENTION

In JP 2004-226068 A, there is disclosed a cartridge incorporating a DNA chip for simultaneous detection of a multitude of DNAs. Such a DNA chip as described is useful for simultaneous measurement of a multitude of measurement targets, however, in case the measurement targets are few in number, probes other than those in use will be useless.

In analysis of SNPs (single nucleotide polymorphisms), a high S/N ratio, such as, for example, detection of a difference by one base out of 25 bases is required. In such a case, use of Invader (trade name) process is higher in practicality, and less expensive than hybridization.

It is an object of the invention to make full use of a technology associated with the chemical reaction cartridge, thereby providing a cartridge adaptable to various measurement forms.

In accordance with one aspect of the invention, there is provided a chemical reaction cartridge capable of causing deformation to occur thereto upon application of an external force thereto, and transferring or sealing substances contained therein, thereby causing chemical reaction to proceed, said cartridge comprising a sample holder for receiving a sample from outside, a separation section for separating the sample held in the sample holder to be distributed into a plurality of paths according to the deformation occurring to the cartridge, reactors for causing portions of the sample, separated in the separation section, to undergo the chemical reaction, individually, and a measurement section for executing measurement on respective reaction products resulting from the chemical reaction taking place in the respective reactors.

With the chemical reaction cartridge according to the invention, a procedure for chemical treatment on the sample is pre-specified by a construction of the cartridge, so that stable chemical treatment can be implemented. With this chemical reaction cartridge, the sample is not limited to a liquid provided that it has fluidity The sample may be a gel or a gas. There is no limitation to the type of the chemical reaction in the respective reactors. There is no limitation to the content of the measurement or a method of the measurement, adopted in the measurement section.

In the measurement section, generation amounts of the respective reaction products may be measured.

In the reactors, DNA amplification or enzymatic reaction may be executed.

In the reactors, any of chemical reaction types including redox reaction, catalysis, optical reaction, crosslinking reaction, polymerization, and chemical modification may be executed.

In the measurement section, any of methods for measurement, including fluorometry, color measurement, absorbance measurement, luminescence measurement, redox current measurement based on volt-ampere characteristics, electrophoresis measurement, and chromatography may be executed.

In the reactors, any of methods including the PCR method, LAMP method, NASBA method, RCA method, ICAN method, and real-time PCR method may be adopted.

The sample may be a biopolymer, however, the sample needs to contain a chemical substance causing the chemical reaction to take place in the reactors.

In the reactors, different reactions may be simultaneously executed on identical samples. In this case, identity as well as simultaneity of the sample is ensured.

The chemical reaction cartridge according to the invention may further comprise a pretreatment unit for applying pretreatment to the sample held in the sample holder.

Optical paths for guiding light may be provided between the measurement section, and the outside of the cartridge. In such a case, the optical paths may be made up of either a constituent material of the cartridge, or material different from the constituent material.

The chemical reaction cartridge according to the invention may be a chemical reaction cartridge capable of causing deformation to occur thereto upon application of an external force thereto, and transferring or sealing substances contained therein, thereby causing chemical reaction to proceed, comprising at least two first wells, and second wells, respectively, set at different temperatures, respectively, wherein DNA amplification is executed by causing respective samples to be reciprocated between the first wells, and the second wells, respectively, in response to the deformation of the cartridge.

With this chemical reaction cartridge, there may be provided not less than three of the first wells, and second wells, respectively, between which the respective samples are reciprocated respectively.

The chemical reaction cartridge according to the invention may be a chemical reaction cartridge capable of causing deformation to occur thereto upon application of an external force thereto, and transferring or sealing substances contained therein, thereby causing chemical reaction to proceed, comprising a transfer section for causing samples to be transferred according to the deformation of the cartridge, and flow paths for electrophoresis, intersecting respective transfer direction of the samples in the transfer section to thereby receive the respective samples being transferred.

With this chemical reaction cartridge, amounts of the respective samples received in the respective flow paths for the electrophoresis, and receiving positions of the respective samples can be controlled with high precision, so that it is possible to enhance precision of the electrophoresis.

In accordance with another aspect of the invention, there is provided a method of using a chemical reaction cartridge capable of causing deformation to occur thereto upon application of an external force thereto, and transferring or sealing substances contained therein, thereby causing chemical reaction to proceed, said method comprising the step of providing the cartridge with a sample holder for receiving a sample from outside, a separation section for separating the sample held in the sample holder to be distributed into a plurality of paths according to the deformation occurring to the cartridge, reactors for causing portions of the sample, separated in the separation section, to undergo the chemical reaction, individually, and a measurement section for executing measurement on respective reaction products resulting from the chemical reaction taking place in the respective reactors, thereby executing injection of the sample, the reaction, and the measurement, and the step of discarding the cartridge.

With this method of using the chemical reaction cartridge, the procedure for the chemical treatment on the sample is pre-specified by the construction of the cartridge, so that stable chemical treatment can be implemented. Further, since the processing is carried out in a closed system, and the cartridge is discarded after use, high safety is ensured, and post-treatment is unnecessary. The sample is not limited to a liquid provided that it has fluidity. The sample may be a gel or a gas. There is no limitation to the type of the chemical reaction in the respective reactors. There is no limitation to the content of the measurement or the method of the measurement, adopted in the measurement section.

The method of using the chemical reaction cartridge, according to the invention, may be a method of using a chemical reaction cartridge capable of causing deformation to occur thereto upon application of an external force thereto, and transferring or sealing substances contained therein, thereby causing chemical reaction to proceed, said method comprising the step of providing the cartridge with at least two first wells, and second wells, respectively, to thereby set the first wells, and the second wells to different temperatures, respectively, and the step of causing respective samples to be reciprocated between the first wells, and the second wells, respectively, in response to the deformation of the cartridge, thereby executing DNA amplification.

With this chemical reaction cartridge as well, there may be provided not less than three of the first wells, and the second wells, respectively, set at different temperatures, respectively, the respective samples being reciprocated therebetween, respectively.

With the chemical reaction cartridge according to the invention, the procedure for chemical treatment on the sample is pre-specified by the construction of the cartridge, so that stable chemical treatment can be implemented.

With the chemical reaction cartridge according to the invention, the amounts of the respective samples received in the respective flow paths for the electrophoresis, and the receiving positions of the respective samples can be controlled with high precision, so that it is possible to enhance the precision of the electrophoresis.

Further, with the method of using the chemical reaction cartridge, according to the invention, the procedure for the chemical treatment on the sample is pre-specified by the construction of the cartridge, so that stable chemical treatment can be implemented.

BRIEF DESCRIPTION OF THE DRAWINGS

FIG. 1 is a view showing a construction of a chemical reaction cartridge according to Working Example 1 of the invention, in which FIG. 1(A) is a plan view of the cartridge according to Working Example 1, and FIG. 1(B) is a sectional view showing a section of the cartridge, taken along wells and flow paths in FIG. 1(A);

FIG. 3 is a view showing a construction of a chemical reaction cartridge according to Working Example 2 of the invention, in which

FIG. 4 is a view showing a construction of a chemical reaction cartridge according to Working Example 3, in which

FIG. 5 is a view showing a construction of a chemical reaction cartridge according to Working Example 4, in which

FIG. 7 is a view showing a construction of a chemical reaction cartridge according to Working Example 5, in which

FIG. 9 is a view showing a case where optical waveguides are formed in the cartridge, in which

PREFERRED EMBODIMENTS OF THE INVENTION

Embodiments of a chemical reaction cartridge according to the invention are described hereinafter.

WORKING EXAMPLE 1

A chemical reaction cartridge according to Working Example 1 of the invention is described hereinafter with reference to FIGS. 1 and 2. Working Example 1 represents a cartridge wherein PCR (polymerase chain reaction) amplification is executed to thereby analyze PCR by-products by electrophoresis.

FIG. 1(A) is a plan view of the chemical reaction cartridge according to Working Example 1, and FIG. 1(B) is a sectional view showing a section of the cartridge, taken along wells and flow paths in FIG. 1(A).

As shown in FIG. 1(B), a vessel of the cartridge according to Working Example 1 comprises a substrate 1, and an elastic member 2 overlaid on the substrate 1. Recesses, each in a predetermined shape, depressed toward the top surface of the elastic member 2 (an upper surface thereof, in FIG. 1(B)) are formed in the back surface of the elastic member 2 (the underside surface thereof, in FIG. 1(B)). The recesses create space between the substrate 1, and the elastic member 2, and as shown in FIGS. 1A, 1B, there are formed a well 21 for receiving a sample, a well 22 for pre-holding a liquid solvent, a well 23 for mixing the sample with the liquid solvent, wells 31, 32, 33, for executing PCR amplification, wells 31a, 32a, 33a, connected with the wells 31, 32, 33, respectively, an injection path 24 for injecting the sample into the well 21, a flow path 25 interconnecting the well 21, and the well 23, a flow path 26 interconnecting the well 22, and the well 23, a flow path 27 interconnecting the well 23, and the well 31, a flow path 28 interconnecting the well 23, and the well 32, and a flow path 29 interconnecting the well 23, and the well 33.

Further, flow paths 41, 42, 43, connected to the wells 31, 32, 33, respectively, are formed as the respective recesses of the elastic member 2.

Figure 1:
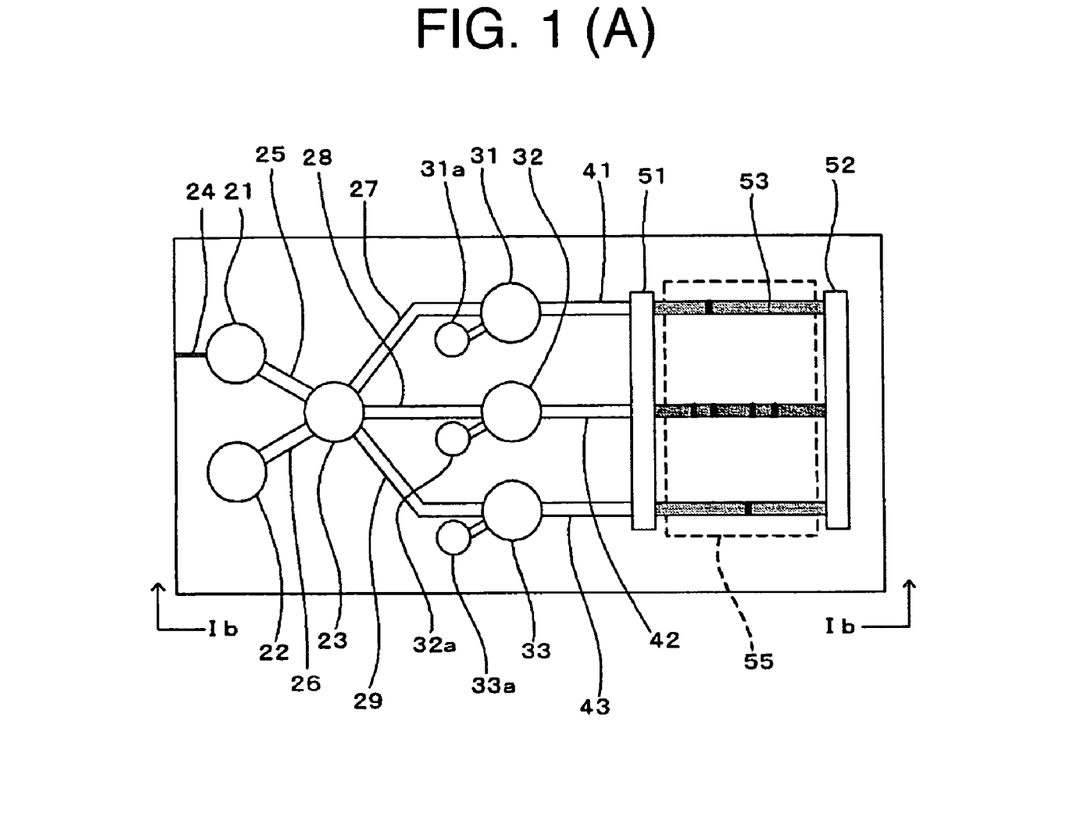

As shown in FIG. 1, electrodes 51, 52, each extended in a direction orthogonal to the flow paths 41, 42, 43, respectively, are embedded in the cartridge. Outlet electrodes 51a, 52a are connected to the electrodes 51, 52, respectively. Respective portions of the flow paths 41, 42, 43, corresponding to a region 55 sandwiched between the electrodes 51, 52, are filled up with a gel 53. Analysis by electrophoresis is executed in the region 55 as described later.

Next, there is described hereinafter an analysis method using the cartridge according to Working Example 1.

A sample is injected into the well 21 via the injection path 24 by use of a syringe, and so forth.

Then, as shown in FIG. 1(B), a roller 6 while kept pressed into contact with the cartridge is rotated rightward, whereupon the elastic member 2 undergoes elastic deformation to cause the sample held in the well 21, and the liquid solvent held in the well 22 to reach the well 23 via the flow paths 25, 26, respectively, thereby mixing the sample with the liquid solvent.

Upon further rotation of the roller 6, a mixed liquid is branched into the flow paths 27, 28, 29, respectively, to thereby reach the wells 31, 32, 33, respectively. Further, at this point in time, a primer with specific DNA attached thereto, and DNA synthesis enzyme, pre-held in the wells 31a, 32a, 33a, respectively, are caused to flow into the wells 31, 32, 33, respectively.

Next, temperatures in the wells 31, 32, 33, respectively, are controlled, thereby executing amplification in respective specific DNA regions.

Then, PCR by-products as amplified in the wells 31, 32, 33, respectively, are transferred to the flow paths 41, 42, 43, respectively, by the roller 6. The PCR by-products are transferred as far as a position in the vicinity of the electrode 51, in the region 55 incorporating the respective portions of the flow paths 41, 42, 43, filled up with the gel 53.

Subsequently, a voltage is applied across the electrode 51 as a negative electrode, and the electrode 52 as a positive electrode via a drawing electrode 51a and a drawing electrode 52a, to thereby cause the PCR by-products to undergo electrophoresis.

With a fluorescent marker in a state emitting light by the agency of excited light, the result of the electrophoresis can be analyzed by picking up an image of the region 55 shown in FIG. 1(A). Further, for picking up the image of the region 55, use can be made of, for example, the reader disclosed in JP 2003-028799 A, and so forth. With the reader, a camera for picking up an image of a DNA chip, and an excited light source can double as an instrument for use in conducting an analysis of the result of the electrophoresis.

The cartridge is discarded after the analysis.

Thus, with the cartridge according to Working Example 1, a procedure for chemical treatment is pre-specified by a construction of the cartridge, so that there occurs no difference in result, due to difference in skill among individuals, thereby enabling reliability of the analysis to be enhanced. If driving of the roller 6 is automated, this will always ensure processing under a constant condition. Furthermore, since the processing is carried out in a closed system, mixing of viruses into the cartridge, and leakage thereof, to outside, can be prevented, so that it is possible to ensure reliability of the analysis, and safety at the time when the cartridge is put to use.

With the cartridge according to Working Example 1, it is possible to conduct an analysis on a small number of specified DNA unsuited for hybridization at a low cost, and further, the conventional reader for the DNA chip can be utilized.

With the cartridge according to Working Example 1, the analysis is conducted on 3 varieties of DNA, however, the number of analysis targets can be optionally selected. For example, on the assumption that the region (an image photograph region) 55 for the electrophoresis is about 10 mm in width, and the limit of a pitch between the respective flow paths is about 0.5 mm, the analysis on up to about 20 varieties of DNA becomes possible.

Further, in general, an electrophoresis method, in its one aspect, is unstable in positional reproducibility, so that it is desirable to provide a flow path, corresponding to one channel, and so forth, for control by use of a known DNA. For example, a control DNA designed such that an electrophoresis pattern will become ladder-like according to a DNA amount may be kept held in the cartridge, and the PCR amplification and the electrophoresis may be applied to the control DNA as with the sample.

Figure 2:
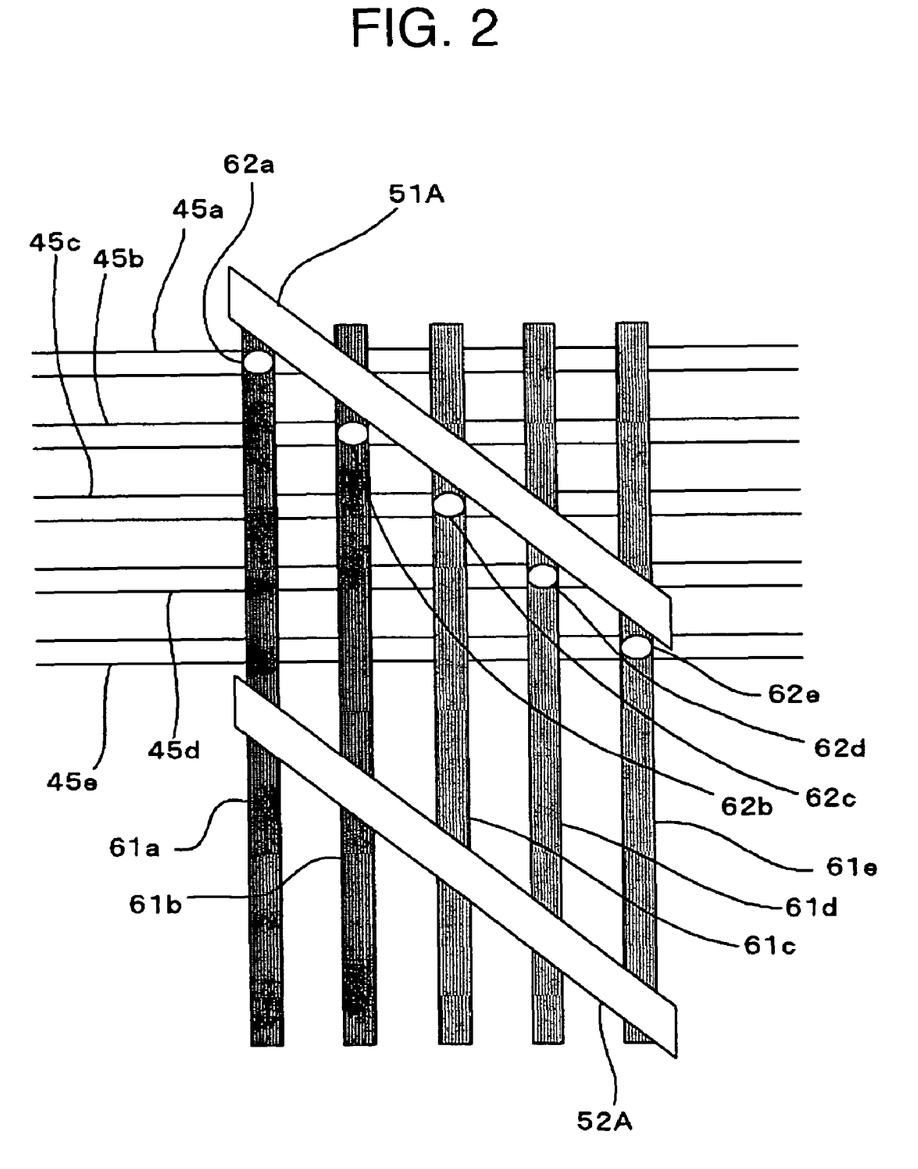
FIG. 2 is a plan view showing a construction example of the cartridge, for evenly controlling amounts of samples undergoing electrophoresis.

FIG. 2 is a plan view showing a construction example of the cartridge, for evenly controlling amounts of samples undergoing the electrophoresis.

With the cartridge shown in FIG. 2, flow paths 45a to 45e, in which PCR by-products are transferred, respectively, and flow paths 61a to 61e, which are filled up with a gel, respectively, are formed so as to intersect each other. A roller is driven in a direction along the flow paths 45a to 45e. At respective intersections of the flow paths 45a to 45e, and the flow paths 61a to 61e, there are formed connection holes 62a to 62e for connecting both the flow paths together, in the direction of thickness of the cartridge.

When the PCR by-products are transferred rightward in the flow paths 45a to 45e, respectively, by the roller, the PCR by-products reach the flow paths 61a to 61e, respectively, via the respective connection holes 62a to 62e. Thereafter, a voltage is applied across the electrodes 51A, 52A, thereby causing the PCR by-products to undergo the electrophoresis.

In this case, respective amounts of the PCR by-products, delivered to the flow paths 61a to 61e, can be equalized by the respective connection holes 62a to 62e. Further, since positions of the PCR by-products are prescribed by the connection holes 62a to 62e, respectively, it is possible to enhance positional precision at the start time of the electrophoresis. Hence, the analysis with higher precision is enabled.

WORKING EXAMPLE 2

A chemical reaction cartridge according to Working Example 2 of the invention is described hereinafter with reference to FIG. 3. Working Example 2 represents a case of application of the cartridge to the Invader (trade name) process developed by Third Wave Technologies. The Invader process is a process of detecting genotypic variation, whereby a DNA sample is mixed with an Invader reagent for incubation to thereby undergo Invader reaction before measurement with fluorescent light. The Invader process is also used for the analysis of SNPs (single nucleotide polymorphisms), and so forth.

Figure 3A:
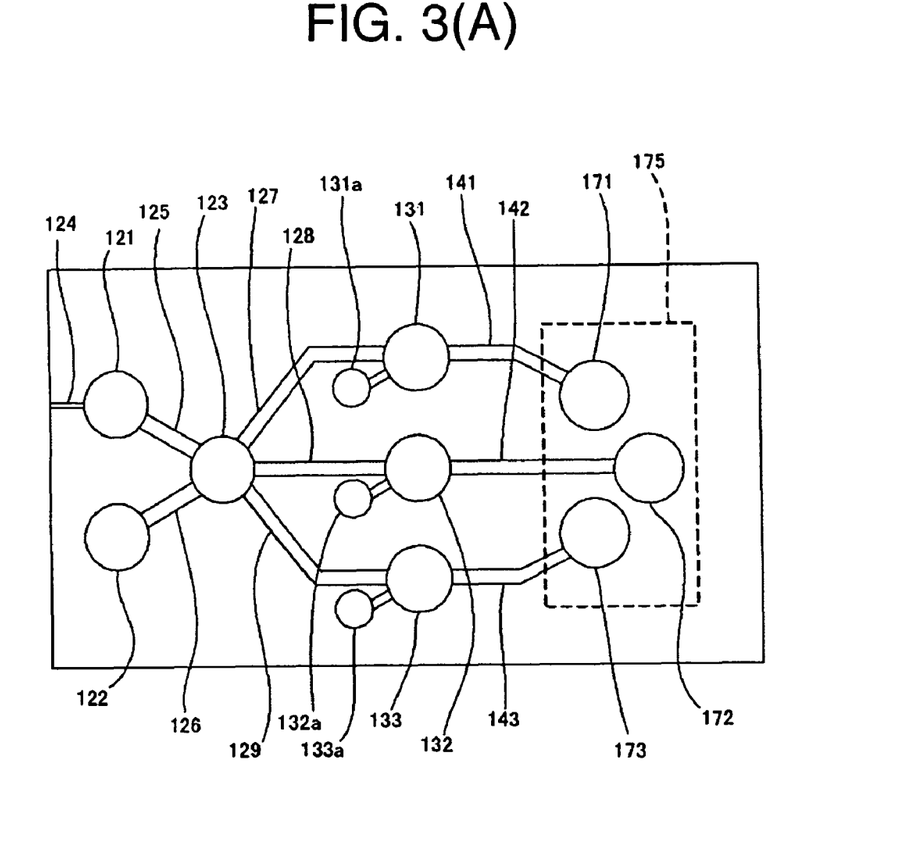
FIG. 3(A) is a plan view of the cartridge according to Working Example 2.
Figure 3B:
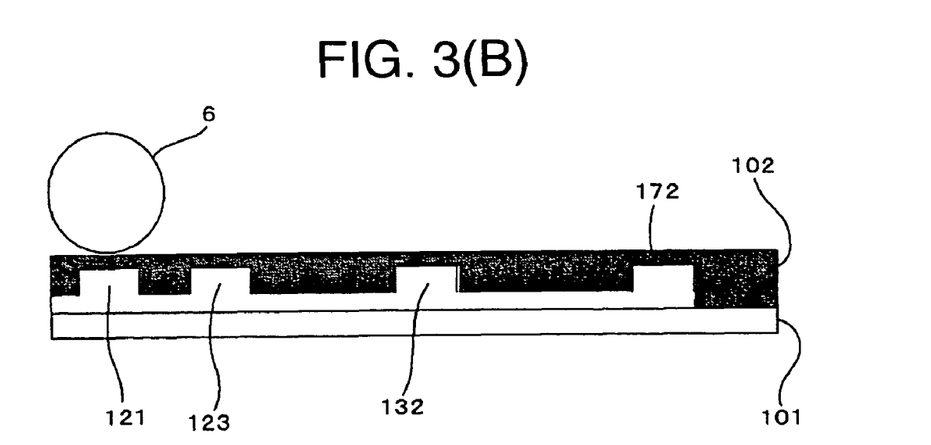
FIG. 3(B) is a sectional view, showing a section of the cartridge, taken along wells and flow paths, shown in FIG. 3(A)

FIG. 3(A) is a plan view of the cartridge according to Working Example 2, and FIG. 3(B) is a sectional view, showing a section of the cartridge, taken along wells and flow paths, shown in FIG. 3(A).

As shown in FIG. 3(B), a vessel of the cartridge according to Working Example 2 comprises a substrate 101, and an elastic member 102 overlaid on the substrate 101.

Recesses, each in a predetermined shape, depressed toward the top surface of the elastic member 102 (an upper surface thereof, in FIG. 3(B)) are formed in the back surface of the elastic member 102 (the underside surface thereof, in FIG. 3(B)). The recesses create space between the cartridge substrate 101, and the elastic member 102, and as shown in FIGS. 3A, 3B, there are formed a well 121 for receiving a sample, a well 122 for pre-holding a liquid solvent, a well 123 for mixing the sample with the liquid solvent, wells 131, 132, 133, for executing the PCR amplification, respectively, wells 131a, 132a, 133a, connected with the wells 131, 132, 133, respectively, an injection path 124 for injecting the sample into the well 121, a flow path 125 interconnecting the well 121, and the well 123, a flow path 126 interconnecting the well 122, and the well 123, a flow path 127 interconnecting the well 123, and the well 131, a flow path 128 interconnecting the well 123, and the well 132, and a flow path 129 interconnecting the well 123, and the well 133.

Further, flow paths 141, 142, 143, connected to the wells 131, 132, 133, respectively, and wells 171, 172, 173, connected to respective terminals of the flow paths 141, 142, 143, are formed as the respective recesses of the elastic member 102.

Next, there is described hereinafter an analysis method using the cartridge according to Working Example 2.

A sample is injected into the well 121 via the injection path 124 by use of a syringe, and so forth.

Then, as shown in FIG. 3(B), a roller 6 while kept pressed into contact with the cartridge is rotated rightward, whereupon the elastic member 102 undergoes elastic deformation to cause the sample held in the well 121, and the liquid solvent held in the well 122 to reach the well 123 via the flow paths 125, 126, respectively, thereby mixing the sample with the liquid solvent.

Upon further rotation of the roller 6, a mixed liquid is branched into the flow paths 127, 128, 129, respectively, to thereby reach the wells 131, 132, 133, respectively. Further, at this point in time, allele oligomer (invader oligomer), and DNA synthesis enzyme, pre-held in the wells 131a, 132a, 133a, respectively, are caused to flow into the wells 131, 132, 133, respectively.

In the wells 131, 132, 133, respectively, the Invader process proceeds due to the incubation.

Subsequently, respective reaction products in the wells 131, 132, 133 are transferred via the flow paths 141, 142, 143, respectively, by the roller 6, to be thereby shifted into the wells 171, 172, 173, respectively.

Then, an image of a region 175 shown in FIG. 3(A) is photographed with the use of a camera to thereby carry out an analysis.

In this case, with a fluorescent marker in a state emitting light by the agency of excited light, the region 175 is photographed by the camera, thereby executing an analysis on amounts of DNA contained in the wells 171, 172, 173, respectively. Further, for photographing the region 175, use can be made of, for example, the reader disclosed in JP 2003-028799 A, and so forth. With the reader, the camera for picking up the image of the DNA chip, and the excited light source can double as the instrument for use in conducting the analysis described.

The cartridge is discarded after the analysis.

Thus, with the cartridge according to Working Example 2, a procedure for chemical treatment is pre-specified by the construction of the cartridge, so that there occurs no difference in result, due to difference in skill among individuals, thereby enabling reliability of the analysis to be enhanced. If driving of the roller 6 is automated, this will always ensure processing under a constant condition. Furthermore, since the processing is carried out in a closed system, mixing of viruses into the cartridge, and leakage thereof, to the outside, can be prevented, so that it is possible to ensure the reliability of the analysis, and safety at the time when the cartridge is put to use.

With the cartridge according to Working Example 2, it is possible to conduct an analysis on a small number of specified DNA unsuited for hybridization at a low cost, and further, the conventional reader for the DNA chip can be utilized.

With the cartridge according to Working Example 2, the analysis is conducted on 3 varieties of DNA, however, the number of analysis targets can be optionally selected. For example, on the assumption that an image photograph region is about 10 mm in width, and the limit of a pitch between the respective flow paths is about 0.5 mm, the analysis on up to about 20 varieties of DNA becomes possible.

WORKING EXAMPLE 3

A chemical reaction cartridge according to Working Example 3 of the invention is described hereinafter with reference to FIG. 4.

Working Example 3 represents a case of application of the cartridge to a real-time PCR method. The real-time PCR method is a method whereby amounts of PCR amplification are monitored in real time to thereby execute an analysis, which is excellent in rapidity and quantification while requiring no electrophoresis. With this method, a sample of unknown concentration is subjected to a temperature cycle on a given condition to cause PCR amplification, thereby finding the number of the cycles until a given amount of amplification products is obtained. If there is prepared beforehand a working curve indicating the number of cycles applied to DNA of a known amount, obtained by dilution in stages, until an amount of amplification products reach an identical amount on an identical condition, it is possible to measure an amount of DNA in the sample on the basis of the working curve.

Figure 4A:
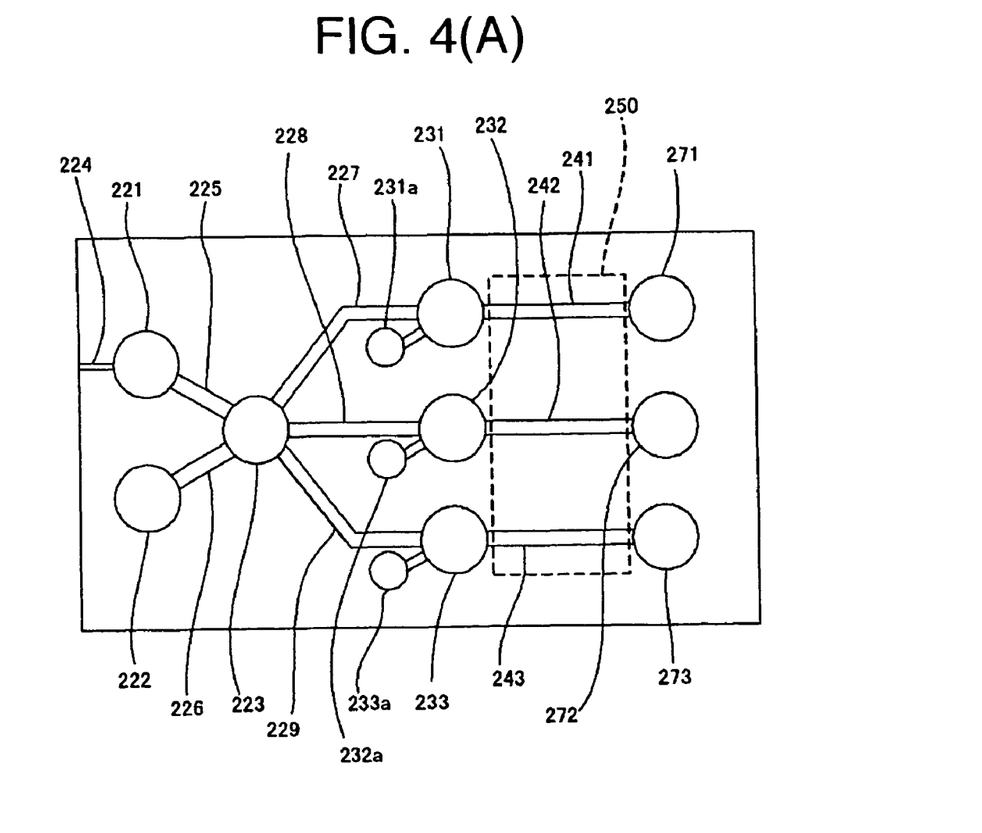
FIG. 4(A) is a plan view of the cartridge according to Working Example 3.
Figure 4B:
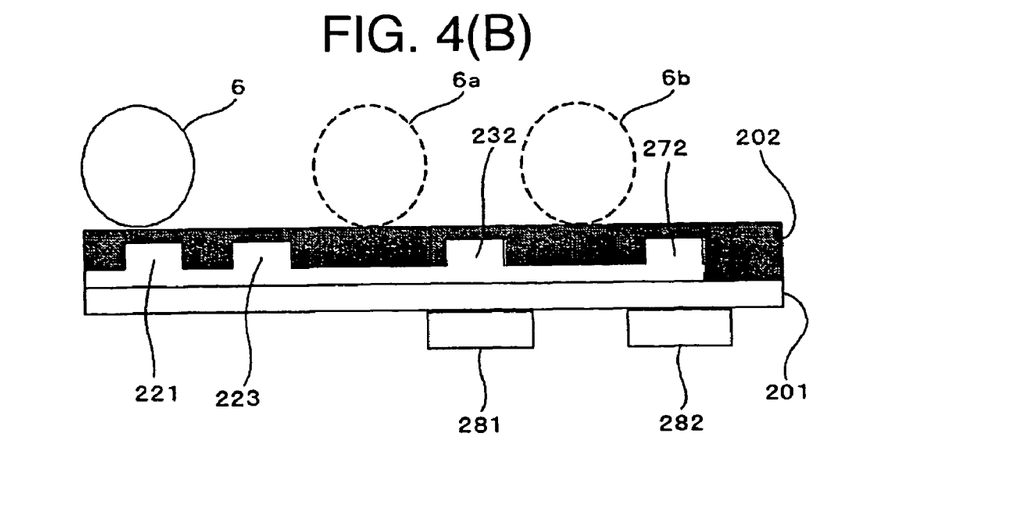
FIG. 4(B) is a sectional view, showing a section of the cartridge, taken along wells and flow paths, shown in FIG. 4(A)

FIG. 4(A) is a plan view of the cartridge according to Working Example 3, and FIG. 4(B) is a sectional view, showing a section of the cartridge, taken along wells and flow paths, shown in FIG. 4(A).

As shown in FIG. 4(B), a vessel of the cartridge according to Working Example 3 comprises a substrate 201, and an elastic member 202 overlaid on the substrate 201.

Recesses, each in a predetermined shape, depressed toward the top surface of the elastic member 202 (an upper surface thereof, in FIG. 4(B)) are formed in the back surface of the elastic member 202 (the underside surface thereof, in FIG. 4(B)). The recesses create space between the cartridge substrate 201, and the elastic member 202, and as shown in FIGS. 4A, 4B, there are formed a well 221 for receiving a sample, a well 222 for pre-holding a liquid solvent, a well 223 for mixing the sample with the liquid solvent, wells 231, 232, 233, for executing the PCR amplification, wells 231a, 232a, 233a, connected with the wells 231, 232, 1233, respectively, an injection path 224 for injecting the sample into the well 221, a flow path 225 interconnecting the well 221, and the well 223, a flow path 226 interconnecting the well 222, and the well 223, a flow path 227 interconnecting the well 223, and the well 231, a flow path 228 interconnecting the well 223, and the well 232, and a flow path 229 interconnecting the well 223, and the well 233.

Further, wells 271, 272, 273, for executing the PCR amplification, respectively, a flow path 241 interconnecting the well 231, and the well 271, a flow path 242 interconnecting the well 232, and the well 272, and a flow path 243 interconnecting the well 233, and the well 273 are formed as the respective recesses of the elastic member 202.

Next, there is described hereinafter an analysis method using the cartridge according to Working Example 3.

A sample is injected into the well 221 via the injection path 224 by use of a syringe, and so forth.

Then, as shown in FIG. 4(B), a roller 6 while kept pressed into contact with the cartridge is rotated rightward, whereupon the elastic member 202 undergoes elastic deformation to cause the sample held in the well 221, and the liquid solvent held in the well 222 to reach the well 223 via the flow paths 225, 226, respectively, thereby mixing the sample with the liquid solvent.

Upon further rotation of the roller 6, a mixed liquid is branched into the flow paths 227, 228, 229, respectively, to thereby reach the wells 231, 232, 233, respectively. Further, at this point in time, a primer with specific DNA attached thereto, DNA synthesis enzyme, and a real-time detection probe, pre-held in the wells 231a, 232a, 233a, respectively, are caused to flow into the wells 231, 232, 233, respectively, to be mixed with the mixed liquid.

As a method of adding the detection probe, there are known the intercalater method, and so forth. With this method, an intercalater {for example, SYBR (trade name) Green 1} emitting fluorescent light upon binding to duplex DNA is used as the detection probe. The intercalater binds to duplex DNA synthesized by PCR reaction and emits fluorescent light by irradiation with excited light. By detection of intensity of the fluorescent light, it is possible to monitor a generation amount of an amplification product. Further, it is also possible to measure melting temperature of amplified DNA.

As shown in FIG. 4(B), temperatures in the wells 231, 232, and 233, respectively, are controlled by a temperature controller 281 using a heater or a Peltier element, and temperatures in the wells 271, 272, and 273 are controlled by a temperature controller 282 using a heater or a Peltier element so as to be at respective given temperatures (for example, at 60° C. and 90° C., respectively).

By driving the roller 6, respective PCR by-products reciprocate between the well 231 and the well 271, between the well 232 and the well 272, and between the well 233 and the well 273 according to a predetermined cycle. In this case, use may be made of two rollers 6a, 6b, indicated by respective dotted lines.

The respective PCR by-products reciprocating between those wells communicating with each other are photographed by a camera while in transit through the flow paths 241, 242, 243, respectively, whereupon amounts of respective amplification products are measured in real time based on a quantity of fluorescent light. A region 250 shown in FIG. 4(A) indicates a region photographed by the camera.

Further, for photographing the region 250, use can be made of, for example, the reader disclosed in JP 2003-028799 A, and so forth. With the reader, the camera for picking up the image of the DNA chip, and the excited light source can double as the instrument for use in conducting the analysis described.

The cartridge is discarded after the analysis.

Thus, with the cartridge according to Working Example 3, the procedure for the chemical treatment is pre-specified by the construction of the cartridge, so that there occurs no difference in result, due to difference in skill among individuals, thereby enabling reliability of the analysis to be enhanced. If driving of the roller 6 is automated, this will always ensure processing under the constant condition. Furthermore, since the processing is carried out in the closed system, mixing of viruses into the cartridge, and leakage thereof, to the outside, can be prevented, so that it is possible to ensure the reliability of the analysis, and safety at the time when the cartridge is put to use.

With the cartridge according to Working Example 3, it is possible to conduct an analysis on a small number of specified DNA unsuited for hybridization at a low cost, and further, the conventional reader for the DNA chip can be utilized.

With the cartridge according to Working Example 3, the analysis is conducted on 3 varieties of DNA, however, the number of analysis targets can be optionally selected. For example, on the assumption that the photographing region is about 10 mm in width, and the limit of the pitch between the respective flow paths is about 0.5 mm, the analysis on up to about 20 varieties of DNA becomes possible.

With the cartridge according to Working Example 3, there is described a case of application to a cycle with a temperature condition varying in two steps, however, it is possible to set not less than three steps of temperature conditions.

EXAMPLE 4

FIG. 5 shows a construction of a chemical reaction cartridge according to Working Example 4 of the invention, corresponding to temperature conditions varying in three steps.

Figure 5A:
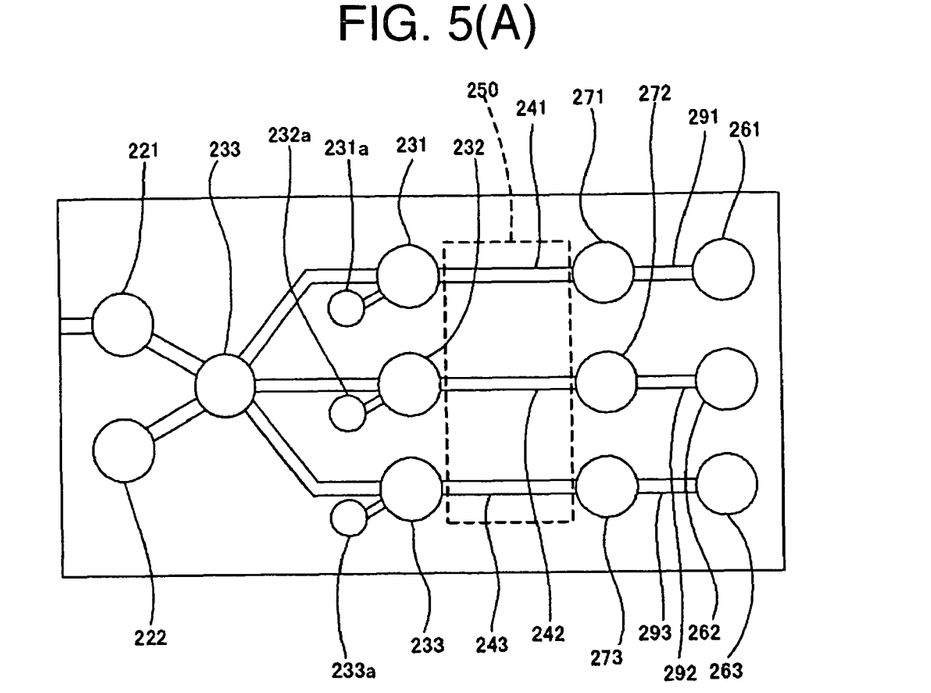
FIG. 5(A) is a plan view of the chemical reaction cartridge according to Working Example 4.
Figure 5B:
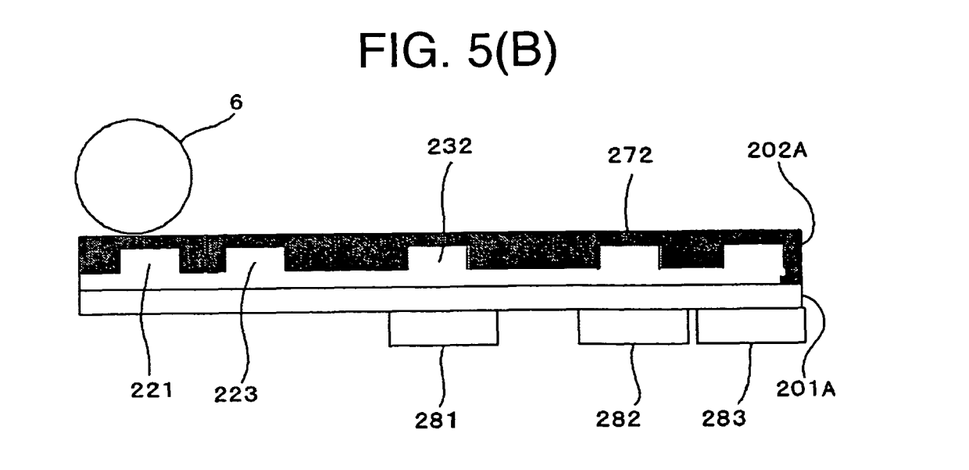
FIG. 5(B) is a sectional view showing a section of the cartridge, taken along wells and flow paths in FIG. 5(A)

FIG. 5(A) is a plan view of the chemical reaction cartridge according to Working Example 4, and FIG. 5(B) is a sectional view showing a section of the cartridge, taken along wells and flow paths in FIG. 5(A). There will be described hereinafter points where the cartridge according to Working Example 4 differs from that shown in FIG. 4.

As shown in FIG. 5(B), the cartridge according to Working Example 4 comprises a substrate 201, and an elastic member 202 overlaid on the substrate 201.

With the cartridge shown in FIG. 5, wells 261, 262, 263, for executing the PCR amplification, respectively, are formed in addition to the cartridge according to Working Example 3. Further, the well 261 is linked with the well 271 via a flow path 291, the well 262 is linked with the well 272 via a flow path 292, and the well 263 is linked with the well 273 via a flow path 293, respectively.

As shown in FIG. 5(B), temperatures in the wells 261, 262, and 263, respectively, are controlled by a temperature controller 283.

Figure 6:
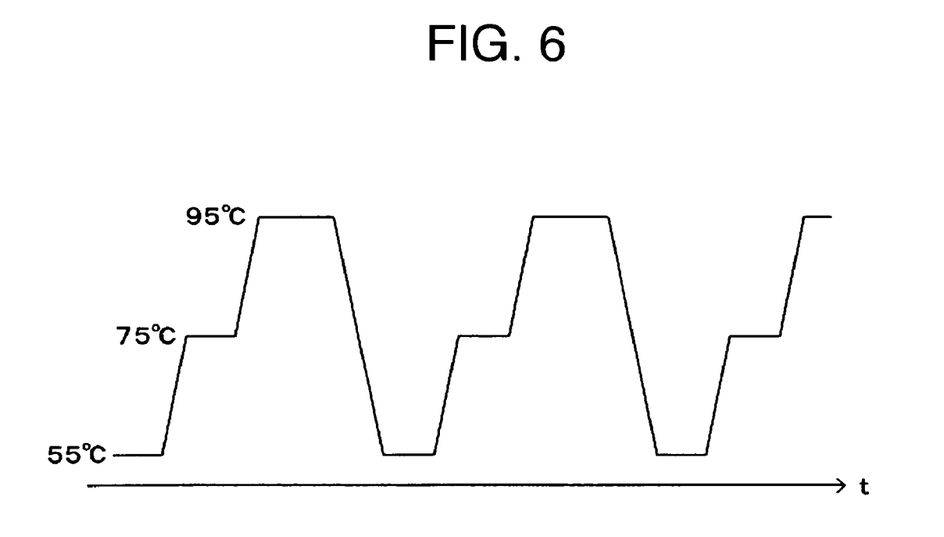
FIG. 6 is a diagram showing an example of a cycle with temperature conditions varying in three steps.

FIG. 6 is a diagram showing an example of a cycle with a temperature condition varying in three steps. With this example, the temperature conditions at 55° C., 75° C., and 95° C., respectively, are specified. For example, by setting the temperature controllers 281, 282, 283, shown in FIG. 5(B), to respective set temperatures at 55° C., 75° C., and 95° C., respective temperatures of the wells corresponding to the respective temperature controllers can be kept at those set temperatures, respectively.

As with the case of the cartridge shown in FIG. 4, while respective PCR by-products are shifted between the respective wells communicating with each other according to the cycle shown in FIG. 6, images in a region 250 are photographed by a camera, thereby enabling amounts of the amplification products to be measured in real time.

WORKING EXAMPLE 5

A chemical reaction cartridge according to Working Example 5 of the invention is described hereinafter with reference to FIG. 7. The cartridge according to Working Example 5 represents an example where the invention is applied to a case where simultaneous measurements are taken on a plurality of samples.

Figure 7A:
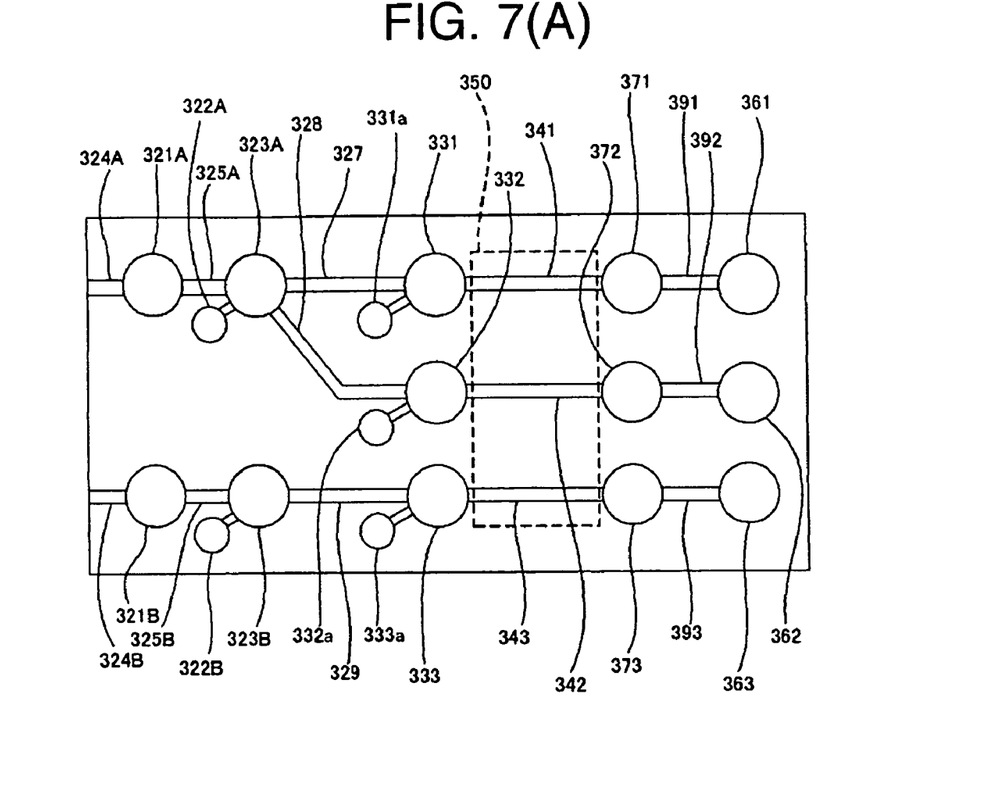
FIG. 7(A) is a plan view of the chemical reaction cartridge according to Working Example 5.
Figure 7B:
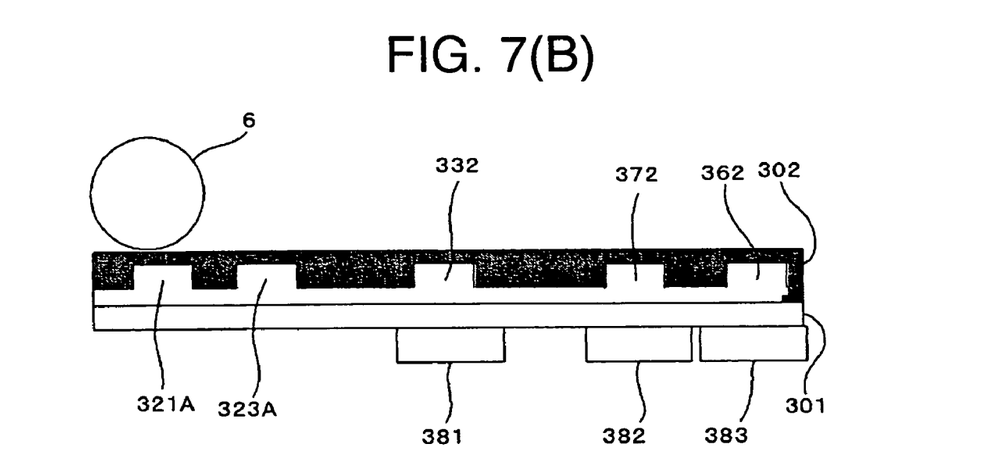
FIG. 7(B) is a sectional view showing a section of the cartridge, taken along wells and flow paths in FIG. 7(A)

FIG. 7(A) is a plan view of the chemical reaction cartridge according to Working Example 5, and FIG. 7(B) is a sectional view showing a section of the cartridge, taken along wells and flow paths in FIG. 7(A).

As shown in FIG. 7(B), the cartridge according to Working Example 5 comprises a substrate 301, and an elastic member 302 overlaid on the substrate 301.

Recesses, each in a predetermined shape, depressed toward the top surface of the elastic member 302 (an upper surface thereof, in FIG. 7(B)) are formed in the back surface of the elastic member 302 (the underside surface thereof, in FIG. 7(B)). The recesses create space between the substrate 301, and the elastic member 302, and as shown in FIGS. 7A, 7B, there are formed wells 321A, 321B, for receiving a sample, respectively, wells 322A, 322B, for pre-holding a liquid solvent, respectively, wells 323A, 323B, for mixing the sample with the liquid solvent, respectively, wells 331, 332, 333, for executing the PCR amplification, respectively, wells 331a, 332a, 333a, linked with the wells 331, 332, 333, respectively, injection paths 324A, 324B, for injecting the sample into the wells 321A, 321B, respectively, a flow path 325A interconnecting the well 321A, and the well 323A, a flow path 325B interconnecting the well 321B, and the well 323B, a flow path 327 interconnecting the well 323A, and the well 331, a flow path 328 interconnecting the well 323A, and the well 332, and a flow path 329 interconnecting the well 323B, and the well 333.

Further, wells 371, 372, 373, for executing the PCR amplification, respectively, wells 361, 362, 363, for executing the PCR amplification, respectively, a flow path 341 interconnecting the well 331, and the well 371, a flow path 342 interconnecting the well 332, and the well 372, and a flow path 343 interconnecting the well 333, and the well 373, a flow path 391 interconnecting the well 361, and the well 371, a flow path 392 interconnecting the well 362, and the well 372, and a flow path 393 interconnecting the well 363, and the well 373 are formed as the respective recesses of the elastic member 302.

Next, there is described hereinafter an analysis method using the cartridge according to Working Example 5.

A sample is injected into the well 321A via the injection path 324A by use of a syringe, and so forth. Another sample is injected into the well 321B via the injection path 324B.

Then, as shown in FIG. 7(B), a roller 6 while kept pressed into contact with the cartridge is rotated rightward, whereupon the elastic member 302 undergoes elastic deformation to cause the sample held in the well 321A, and the liquid solvent held in the well 322A to reach the well 323A to be thereby mixed together. Concurrently, the sample held in the well 321B, and the liquid solvent held in the well 322B are caused to reach the well 323B to be thereby mixed together.

Upon further rotation of the roller 6, a mixed liquid in the well 323A is branched into the flow paths 327, 328, respectively, to thereby reach the wells 331, 332, respectively. Further, at this point in time, a primer with specific DNA attached thereto, and DNA synthesis enzyme, pre-held in the wells 331a, 332a, respectively, are caused to flow into the wells 331, 332, respectively, to be mixed with the mixed liquid.

At the same time, a mixed liquid in the well 323B is caused to reach the well 333 via the flow path 329. At this point in time, a primer with specific DNA attached thereto, and DNA synthesis enzyme, pre-held in the wells 333a, are caused to flow into the well 333 to be mixed with mixed liquid.

As shown in FIG. 7B, temperatures in the wells 331, 332, and 333, respectively, are controlled by a temperature controller 381 using a heater or a Peltier element, temperatures in the wells 371, 372, and 373 are controlled by a temperature controller 382 using a heater or a Peltier element, and temperatures in the wells 361, 362, and 363 are controlled by a temperature controller 383 using a heater or a Peltier element so as to be at respectively given temperatures (for example, on the order of 55° C., 75° C., and 90° C., respectively).

By driving the roller 6, respective PCR by-products are transferred between the well 331 and the well 361 via the well 371, between the well 332 and the well 362 via the well 372, and between the well 333 and the well 363 via the well 373, respectively, according to a predetermined cycle.

The respective PCR by-products being transferred between those wells communicating with each other are photographed by a camera while in transit through the flow paths 341, 342, 343, respectively, whereupon respective amounts of amplification products are measured in real time based on a quantity of the fluorescent light. A region 350 shown in FIG. 7(A) indicates a region photographed by the camera.

Further, for photographing the region 350, use can be made of, for example, the reader disclosed in JP 2003-028799 A, and so forth. With the reader, the camera for picking up the image of the DNA chip, and the excited light source can double as the instrument for use in conducting the analysis described.

The cartridge is discarded after the analysis.

Thus, with the cartridge according to Working Example 5, it is possible to take simultaneous measurements on the plurality of the samples in the same region. A makeup capable of taking the simultaneous measurements on the plurality of the samples can be applied to cartridges adopting other measuring methods such as the electrophoresis, and so forth. Such a makeup is useful particularly at the time of simultaneous amplification of a reference substance called "control" (for example, a fragment of DNA, as a reference, and so forth)

With Working Examples 1 to 5, described hereinbefore, one roller is in use, however, if a plurality of rollers are used as shown in FIG. 4(B), and the liquid as the target of transfer, in such a state as sandwiched between the two rollers, is transferred, this will enable the rollers to be driven in state as-pressed into contact with the cartridge, so that it is possible to implement more reliable transfer while preventing leakage of the liquid as the target of transfer to the outside of a transfer range with reliability. This will be effective particularly in the case where reciprocative transfer is required.

A method of the DNA amplification is not limited to PCR, and the cartridge according to the invention is applicable to any of methods including LAMP, NASBA, RCA, and ICAN methods, and so forth.

The cartridge according to the invention is applicable to any of chemical reaction types including not only the DNA amplification and enzymatic reaction shown in Invader process, but also redox reaction based on volt-ampere characteristics, catalysis, optical reaction (maleimido reaction, and so forth), crosslinking reaction, polymerization, chemical modification, and so forth.

Further, the cartridge according to the invention is applicable to any of methods for measurement or analysis, including not only fluorometry, but also color measurement, absorbance measurement, luminescence measurement, and so forth. It is also possible to measure reduction current by use of the electrodes embedded in the cartridge without the use of a camera. Further, by supplying the reduction current to substances contained in the cartridge, the substances can be changed in color (polyanine, and so forth).

Further, electrophoresis and chromatography can be combined with the above-described measurement using light and current measurement.

Still further, the measurement targets are not limited to biopolymers such as DNA, RNA, protein, glycosyl, metabolite, and so forth, and the cartridge according to the invention is widely applicable to other molecules having chemical reactivity.

With Working Examples 1 to 5, described in the foregoing, there has been shown a makeup in which the sample is subjected to a pretreatment, however, it is also possible to adopt a makeup in which the sample is directly measured without the pretreatment thereof.

Figure 8:
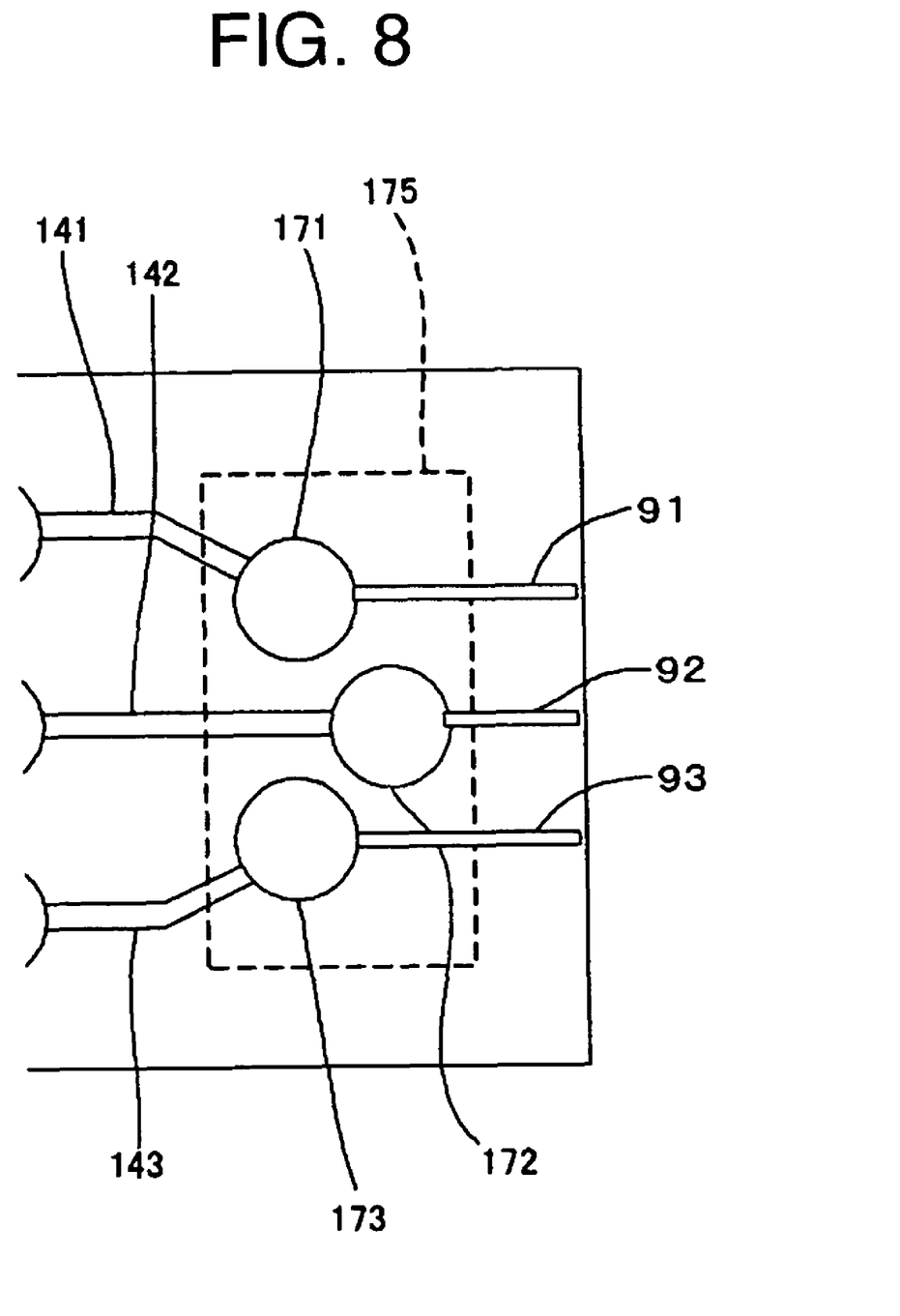
FIG. 8 is a view showing a case where optical waveguides are formed in the cartridge.

FIG. 8 is a view showing a case where optical waveguides are formed in the cartridge. In this case, there is shown a makeup in which the optical waveguides are formed in the cartridge according to Working Example 2.

With this cartridge, respective base ends of optical waveguides 91, 92, 93, formed of, for example, a material greater in refractive index than the elastic member 102, respectively, are connected to the wells 171, 172, 173, respectively, and respective terminals of the optical waveguides 91, 92, 93 are exposed to a side face of the cartridge, as shown in FIG. 8. With the adoption of such a makeup, irradiation with the excited light, and capturing of the fluorescent light can be implemented via the optical waveguides 91, 92, 93, respectively, so that even in the case where the temperature controllers are provided on top of, or underneath the wells 171, 172, 173, respectively, fluorometry can be conducted with the temperature controllers kept in functioning state.

Figure 9A:
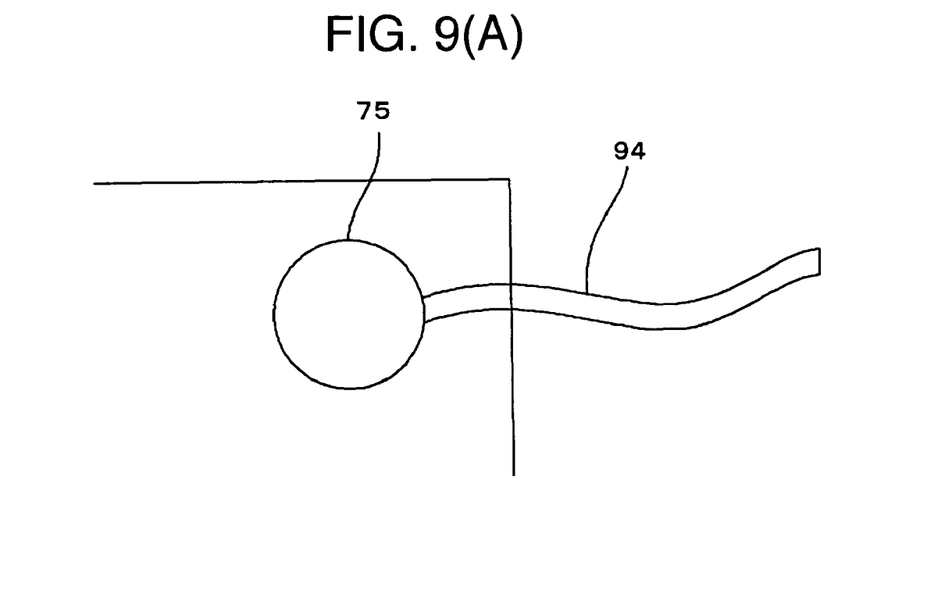
FIG. 9(A) is a view showing a case of using a flexible optical waveguide line.

As shown in FIG. 9(A), a flexible optical waveguide line 94 may be connected to a well 75, and the irradiation with the excited light, and capturing of the fluorescent light may be executed via the optical waveguide line 94.

Figure 9B:
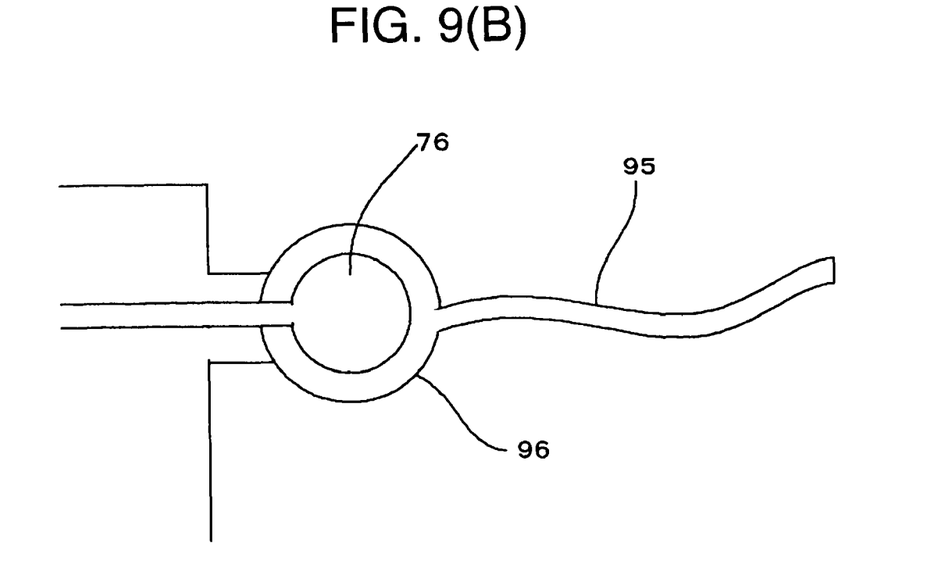
FIG. 9(B) is a view showing a case where a well is formed so as to be projected from the cartridge.

Further, as shown in FIG. 9(B), a well 76 may be formed so as to be projected from the cartridge, and an optical waveguide 96 provided around the well 76 and a flexible optical waveguide line 95 connected to the optical waveguide 96 may be formed integrally with each other.

It is to be pointed that the invention is not limited in scope of application to those working examples described hereinbefore, and that the invention is widely applicable to a chemical reaction cartridge capable of causing deformation to occur thereto upon application of an external force thereto, and transferring substances contained therein, to thereby cause a chemical reaction to proceed, and a method of using the same.

What is claimed is:

1. A chemical reaction cartridge, said cartridge comprising:
    a sample holder for receiving a sample from an outside;
    a separation section for separating the sample held in the sample holder;
    a plurality of paths leading out of said separation section;
    a plurality of reactors in which portions of the sample, separated in the separation section, undergo DNA amplification, individually, each of said plurality of reactors including a first well and a second well, each of said plurality of paths leading to one of said plurality of reactors;
    a measurement section for executing measurement on reaction products resulting from the DNA amplification in the respective reactors;
    an elastic member covering said sample holder, said separation section, said plurality of reactors and said measurement section, and
    a plurality of pairs of temperature controllers, each of said plurality of pairs of temperature controllers corresponding to one of said plurality of reactors, such that said first well and said second well of each of said plurality of reactors can be set to different temperatures,
    wherein the DNA amplification is executed by causing respective samples to be reciprocated between said first well and said second well of each of said plurality of reactors, respectively, in response to the deformation of the cartridge, and
    wherein transfer and sealing of said sample between said sample holder, said separation section, said plurality of reactors and said measurement section is performed by deforming said elastic member by an external force.

2. A chemical reaction cartridge according to claim 1, wherein in the measurement section, generation amounts of the reaction products are measured.

3. A chemical reaction cartridge according to claim 1, wherein said measurement is selected from the group consisting of fluorometry, color measurement, absorbance measurement, luminescence measurement, redox current measurement based on volt-ampere characteristics, electrophoresis measurement, and chromatography.

4. A chemical reaction cartridge according to claim 1, wherein said DNA amplification is selected from the group consisting of polymerase chain reaction (PCR), loop-mediated isothermal amplification (LAMP), nucleic acid sequence based amplification (NASBA), rolling circle amplification (RCA), isothermal and chimeric primer-initiated amplification of nucleic acids (ICAN), and real-time polymerase chain reaction (real-time PCR).

5. A chemical reaction cartridge according to claim 1, wherein the sample is a biopolymer.

6. A chemical reaction cartridge according to claim 1, wherein in the reactors, different chemical reactions are simultaneously executed on identical samples.

7. A chemical reaction cartridge according to claim 1, further comprising a pretreatment unit for applying pretreatment to the sample held in the sample holder.

8. A chemical reaction cartridge according to claim 1, further comprising optical paths for guiding light, said optical paths being provided between the measurement section and the outside of the cartridge.

9. A chemical reaction cartridge capable of being deformed upon application of an external force thereto, and transferring or sealing substances contained therein, thereby causing a chemical reaction to proceed, said cartridge comprising:
    a plurality of transfer flow paths into which a sample is transferred according to the deformation of the cartridge; and
    a plurality of electrophoresis flow paths intersecting a transfer direction of the sample in the plurality of transfer flow paths via connection holes formed in the thickness direction of said cartridge, to thereby receive the sample,
    wherein said plurality of electrophoresis flow paths are substantially perpendicular to said plurality of transfer flow paths, and
    wherein each of said electrophoresis flow paths includes a gel.

10. A chemical reaction cartridge, said cartridge comprising:
    a sample holder for receiving a sample from an outside;
    a separation section for separating the sample held in the sample holder;
    a plurality of paths leading out of said separation section;
    a plurality of reactors in which portions of the sample, separated in the separation section, undergo a chemical reaction, individually, each of said plurality of paths leading to one of said plurality of reactors;

a plurality of transfer flow paths each leading out of one of said plurality of reactors to thereby receive the sample;

a plurality of electrophoresis flow paths intersecting a transfer direction of the sample in the plurality of transfer flow paths via connection holes formed in the thickness direction of said cartridge, each of said plurality of electrophoresis flow paths including a gel;

a measurement section for executing measurement on reaction products resulting from the chemical reaction in the respective reactors; and an elastic member covering said sample holder, said separation section, said plurality of reactors and said measurement section, wherein said plurality of electrophoresis flow paths are substantially perpendicular to said plurality of transfer flow paths, and wherein transfer and sealing of said sample between said sample holder, said separation section, said plurality of reactors and said measurement section is performed by deforming said elastic member by an external force.

11. A chemical reaction cartridge according to claim 10, wherein in the measurement section, generation amounts of the reaction products are measured.

12. A chemical reaction cartridge according to claim 10, wherein said chemical reaction is DNA amplification or an enzymatic reaction.

13. A chemical reaction cartridge according to claim 10, wherein said chemical reaction is selected from the group consisting of a redox reaction, catalysis, an optical reaction, a crosslinking reaction, polymerization, and chemical modification.

14. A chemical reaction cartridge according to claim 10, wherein said measurement is selected from the group consisting of fluorometry, color measurement, absorbance measurement, luminescence measurement, redox current measurement based on volt-ampere characteristics, electrophoresis measurement, and chromatography.

15. A chemical reaction cartridge according to claim 10, wherein said chemical reaction is selected from the group consisting of polymerase chain reaction (PCR), loop-mediated isothermal amplification (LAMP), nucleic acid sequence based amplification (NASBA), rolling circle amplification (RCA), isothermal and chimeric primer-initiated amplification of nucleic acids (ICAN), and real-time polymerase chain reaction (real-time PCR).

16. A chemical reaction cartridge according to claim 10, wherein the sample is a biopolymer.

17. A chemical reaction cartridge according to claim 10, wherein in the reactors, different chemical reactions are simultaneously executed on identical samples.

18. A chemical reaction cartridge according to claim 10, further comprising a pretreatment unit for applying pretreatment to the sample held in the sample holder.

19. A chemical reaction cartridge according to claim 10, further comprising optical paths for guiding light, said optical paths being provided between the measurement section and the outside of the cartridge.

20. A method of using a chemical reaction cartridge, said method comprising:

providing the cartridge with a sample holder for receiving a sample from outside, said cartridge including the sample holder, a separating chamber, a plurality of paths leading out of the separating chamber, a plurality of reactors, an electrophoresis region, and a measurement section, separating the sample held in the sample holder into said plurality of paths leading out of a separating chamber, according to the deformation of the cartridge, individually reacting portions of the sample, separated in the separation section, in said plurality of reactors, using a chemical reaction, each of said plurality of paths leading to one of said plurality of reactors, electrophoresing reaction products resulting from the chemical reaction in a gel in said electrophoresis region of said cartridge, and measuring said reaction products resulting from the chemical reaction in said measurement section, wherein said samples are transferred and sealed upon an external force being applied to an elastic member covering said sample holder, said separating chamber, said plurality of reactors, said electrophoresis region and said measurement section.

* * * * *